United States Patent [19]

Juma

[11] Patent Number: 5,417,226
[45] Date of Patent: May 23, 1995

[54] FEMALE ANTI-INCONTINENCE DEVICE

[76] Inventor: Saad Juma, 4389 Corte de la Forda, San Diego, Calif. 92 130

[21] Appl. No.: 257,273

[22] Filed: Jun. 9, 1994

[51] Int. Cl.⁶ .............................. A61F 5/48; A61F 2/00; A61F 2/02
[52] U.S. Cl. ...................................... 128/885; 600/29; 600/30; 128/DIG. 25
[58] Field of Search ............................ 128/830–841, 128/885, 886, DIG. 25; 604/904; 446/466, 469; 600/29–31

[56] References Cited

U.S. PATENT DOCUMENTS

| | | | |
|---|---|---|---|
| 5,844 | 10/1848 | Schofield | 128/835 |
| 2,155,285 | 4/1939 | Wilkerson | 604/904 |
| 2,510,310 | 6/1950 | Francis | 446/469 |
| 3,372,695 | 3/1968 | Beliveau et al. | |
| 3,646,929 | 3/1972 | Bonnar. | |
| 3,797,478 | 3/1974 | Walsh et al. | |
| 4,209,009 | 6/1980 | Hennig | 128/DIG. 25 |
| 4,920,986 | 5/1990 | Biswas. | |
| 4,961,725 | 10/1990 | Rey | 128/DIG. 25 |
| 5,065,772 | 11/1991 | Cox | 128/836 |
| 5,082,006 | 1/1992 | Jonasson. | |
| 5,090,424 | 2/1992 | Simon et al. | |
| 5,112,306 | 5/1992 | Burton | 128/DIG. 25 |
| 5,352,182 | 10/1994 | Kalb | 600/30 |

OTHER PUBLICATIONS

Nielsen, Kurt K. et al., The urethral plug: a new treatment modality for genuine urinary stress incontinence in women. The Journal of Urology 144:1198–1201 (1990).

Paine–Webber Inc., Vector Securitied International, Inc. Jan. 1994 Prospectus "Uromed" 1 page.

*Primary Examiner*—Michael A. Brown
*Attorney, Agent, or Firm*—Knobbe, Martens, Olson & Bear

[57] ABSTRACT

A female anti-incontinence device is described which includes two flexible discs attached to a flexible stem. The device is inserted into the urethra so that the larger disc occludes the bladder neck during sudden tensing of the abdominal muscles, while the smaller disc remains outside the urethra and prevents migration of the device into the bladder. The device is compact, easy to use, and, since it contains no moving parts, grooves or chambers, there is minimal chance of bacterial colonization and urinary tract infection.

24 Claims, 1 Drawing Sheet

FEMALE ANTI-INCONTINENCE DEVICE

FIELD OF THE INVENTION

This invention relates to a device used for female incontinence. More specifically, it relates to a non-irritating, easy to use device which can be inserted and removed by the individual as desired.

BACKGROUND OF THE INVENTION

Incontinence is a major health problem in the United States and accounts for approximately $10 billion of our annual health care costs. It is estimated that over 10 million individuals suffer from urinary incontinence, 60-70% of which are females. Although there are several types of female incontinence, stress incontinence or stress and urge incontinence is the most common. Stress incontinence is triggered by sudden tensing of the abdominal muscles which occurs during coughing, laughing and certain physical activities. It is caused by abnormalities in the anatomy of the bladder outlet structures, the sphincter and urethra. This problem is most pronounced in the elderly female population due to prolapse of the uterus which distorts the geometry of the bladder neck resulting in a 30% incontinence rate in women over 60 years of age. This problem causes acute embarrassment and inhibits physical and social activity.

Many methods and devices for managing incontinence are currently available. In younger patients, surgery is the method of choice for severe incontinence. However, in older individuals, the risk of complications makes this option impractical. In addition, in mild cases, surgery is not a desirable option. Another common method of managing incontinence is the use of an absorbent pad placed over the urethral opening which is nonhygienic, uncomfortable and does not prevent the involuntary urination. Other less effective incontinence treatment methods include pharmacotherapy, exercise, electrical stimulation and periurethral injections.

Incontinence devices disclosed in the prior art rely mainly on urethral occlusion. Nielsen et al. (*J. Urol.*, (1990) 144:1199–1202) and U.S. Pat. No. 5,082,006 to Jonasson disclose an incontinence device having a shaft with one or more knobs placed along the shaft which occludes the urethra. This design relies on the presence of at least one knob inside the urethra at all times which represents a source of continuous irritation to the patient. In addition, the constant pressure exerted on the walls of the urethra over time will cause urethral dilation, resulting in leakage of urine around the device. This urethral dilation can allow expulsion of the device due to increased bladder pressure, resulting in incontinence.

U.S. Pat. No. 5,090,424 to Simon et al. discloses a flexible urethral plug consisting of a soft inflatable plastic catheter and a transportable liquid. The fluid is introduced through a check valve to inflate the device within the urethra, the bladder neck or the bladder. This device is cumbersome and, since it contains a chamber and a valve, it is impossible to prevent bacterial colonization of the device leading to possible urinary tract infection. In addition, the chamber and valve can malfunction, resulting in balloon deflation and potential leakage of urine. Valve malfunction can also cause either expulsion of the device, resulting in incontinence, or retention of the device which will require medical intervention for its removal.

U.S. Pat. No. 3,372,695 to Beliveau et al. describes an incontinence device having a rod with two retainer portions extending into the bladder to keep the device in position. The continence mechanism of this device is the rod only which will lose its occlusive action over time due to urethral dilation, resulting in leakage of urine around the rod. In addition, this device will irritate the urethra and, since it has moving parts which are impossible to keep clean, there is a risk of bacterial growth and the potential for urinary tract infection. Moreover, valve malfunction can result in either expulsion or retention of the device. U.S. Pat. No. 3,797,478 to Walsh et al. discloses an incontinence device having two inflatable collars and an inflatable stem. Since the inflatable stem occludes and applies constant pressure on the urethra, this will result in urethral wall relaxation and leakage around the device. Moreover, this device requires the use of a syringe to inflate and deflate the collars and stem, making it difficult to use, especially by patients with arthritis. In addition, it is difficult to keep the device free of bacteria.

U.S. Pat. Nos. 3,646,929 to Bonnar and 4,920,986 to Biswas teach intravaginal incontinence devices which can expand to exert pressure on the bladder neck, thus restricting the flow of urine. These methods do not rely on occluding the bladder via insertion of a device into the urethra.

There is a need for a female incontinence device which is simple to use, easy to manufacture, easy to clean and which will not cause irritation to either the urethra or the bladder.

SUMMARY OF THE INVENTION

One embodiment of the present invention is a removable device for preventing involuntary urination in female patients, comprising:
 a flexible stem having a first end and a second end;
 a first flexible disc having a perimeter, a first face and a second face, said first face of said first disc attached to said first end of said stem;
 a second flexible disc having a perimeter, a first face and a second face, said first face of said second disc attached to said second end of said stem; and
 a projection attached to the second face of at least one of said discs.

In another aspect of this embodiment, the projection attached to either said first or said second disc is attached to a string. Alternatively, both projections are attached to a string. The device can also contain a string longitudinally embedded within the stem and the projections, such that the string extends beyond the projections and one of the extensions of the string is removed prior to insertion of the device. Advantageously, the device is made of a flexible, biocompatible material which is resistant to degradation by urine. Preferably, the biocompatible material is an elastic polymer. Most preferably, it is Kraton G, silicone or polyvinylchloride. According to another aspect of this preferred embodiment, the stem is more flexible along its lateral axis than along its longitudinal axis. Advantageously, the diameter of the first disc is greater than the diameter of the second disc. Preferably, the diameter of the first disc is between about 1.0 cm and about 2.0 cm. Most preferably, the diameter of the first disc is 1.5 cm. According to another aspect of this embodiment, the diameter of the second disc is between about 0.5 cm and about 1.5 cm, most preferably 1.0 cm. Further, the discs are attached to the stem at their centers and join the stem at right angles. In accordance with the invention, the length of the stem is between about three and about six centimeters and the diameter of the stem is about 0.4 cm.

Another embodiment of the invention is a method of preventing incontinence in female patients comprising inserting the above-described device into the urethra Preferably, the device is removed prior to voiding of urine. In another aspect of this preferred embodiment, the removing step comprises pulling on the string.

DETAILED DESCRIPTION OF THE INVENTION

The present invention provides a device for the treatment of female incontinence. This device is used in place of other cumbersome methods such as urethral plugs, surgical realignment of the bladder neck and pharmacotherapy. Since the present device relies on occlusion of the bladder neck without urethral occlusion, the device avoids urethral irritation and dilation. Accordingly, the present invention represents a significant improvement over incontinence devices disclosed in the prior art.

The device of the present invention can be made of a any of a variety of biocompatible elastic polymers. Desirable characteristics of the material include softness, flexibility, resistance to degradation by urine and ability to dwell for short periods of time in the urethra and bladder neck. Suitable materials include silicone, Kraton G or Polyvinylchloride (PVC). As used herein, the terms "flexible" and "flexibility" relate to being responsive or adaptable to mechanical deformation as would be encountered when the device is inserted into the urethra and bladder neck. The biocompatible material has a suitable hardness, preferably 25-50 D as measured by a durometer, to impart sufficient flexibility to the device.

Figure 1:
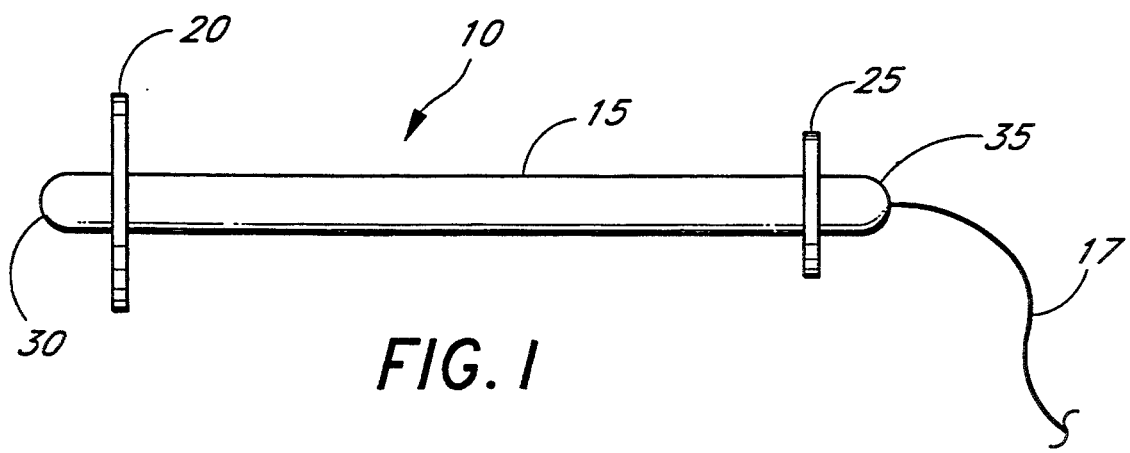
FIG. 1 is a side elevational view of the female anti-incontinence device.
Figure 2:
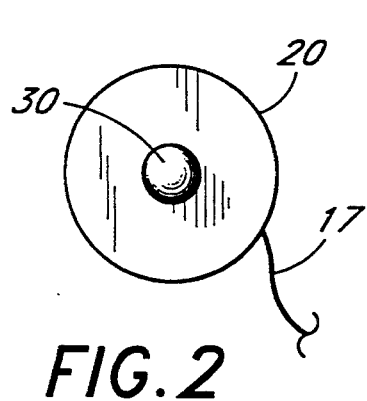
FIG. 2 is an end view from one end of the female anti-incontinence device.
Figure 3:
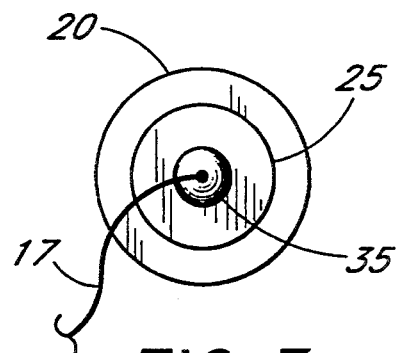
FIG. 3 is an end view from the opposite end of the female anti-incontinence device.

Referring to FIGS. 1-3, the device 10 includes a stem 15 having a diameter of 0.4 cm and a length designed to properly position a disc 20 with respect to the bladder neck of the patient in which the device will be inserted. The length will vary depending on the length of the urethra and other anatomical structures of the patient. Thus, the stem 15 can be produced in a variety of lengths to accommodate anatomical variation. Exemplary stem lengths are in tile range of 2-7 centimeters (cm). Preferred embodiments of the device are produce with stem lengths of 3, 4, 5 and 6 cm. This variation in stem length is due to anatomical variation of the human urethra and is important in proper positioning of the device in the urethra. The stem must not be too long, or the device will reach up too far inside the bladder and will move around, causing irritation by sitting improperly on the bladder neck. However, the stem must be long enough so the device will reach into tile bladder and seal the bladder neck to prevent leakage of urine. The stem can be constructed to be less flexible along the longitudinal axis to allow easy introduction of the device, and more flexible in the lateral direction to allow molding to and flexibility within the urethra, thus avoiding urethral irritation.

Two soft, flexible discs 20, 25 having a radial edge and two substantially planar faces are either molded or attached to the ends of the stem. The discs and the stem can have different rigidities to provide greater functional flexibility to the device. In a preferred embodiment, the stem is more rigid than the discs. The discs can be either the same or different sizes. In a preferred embodiment, disc 20 is between about 1.0 and about 2.0 cm in diameter. In a particularly preferred embodiment, disc 20 has a diameter of 1.5 cm. In a preferred embodiment, disc 25, attached at the end of stem 15 opposite disc 20, has a diameter between about 0.5 and about 1.5 cm. In a particularly preferred embodiment, disc 25 has a diameter of 1.0 cm and stem 15 is attached to the center of discs 20 and 25.

The diameter of the larger disc 20, which forms the seal at the bladder neck, is such that it will form a tight seal, but will not irritate the wall of the bladder. If the disc has a diameter much larger than about 2 cm, it can cause irritation to the bladder and can touch the bladder area known as the trigon, causing the urethra to spasm. In addition, a disc having a larger diameter will cause greater discomfort upon insertion of the device.

A rounded projection or nub 30 between about 0.2 cm and about 1.0 cm in length, most preferably 0.5 cm, and having the same diameter as stem 15 can be attached to disc 20 in order to facilitate introduction of the device into the urethra. Another projection 35 can be attached to disc 25. In a particularly preferred embodiment, projections 30 and 35 are attached to the centers of the faces of discs 20 and 25, respectively, opposite the junction of stem 15. The projections provide a guide for easy insertion of the device into the urethra. The projections preferably have a length between 0.2 and 1 cm. If the projection 30 is much longer than about 1 cm, it can irritate the collapsed wall of the bladder upon insertion. If the projections are smaller than about 0.2 cm, they are less able to serve as noticeable guides for insertion.

Optionally, a string 17 can be attached to either or both projections to allow facilitated removal of the device. In a particularly preferred embodiment, the string can be longitudinally embedded within the stem 15 and projections 30, 35 such that it extends beyond these projections. The user can then remove the string from the end of the device to be inserted into the urethra, while the other end of the string will remain outside the urethra to allow facilitated removal of the device. Thus, the user will have the option of inserting either one end or the other into the urethra, depending on which disc is more effective in occluding the bladder neck.

Discs 20 and 25 can have either the same or different thicknesses. In a preferred embodiment, each disc has a thickness between about 0.1 cm and about 1.5 cm. In a particularly preferred embodiment, each disc has a thickness of 0.1 cm. The thickness of the discs is selected to retain both flexibility and adequate structure.

Figure 4:
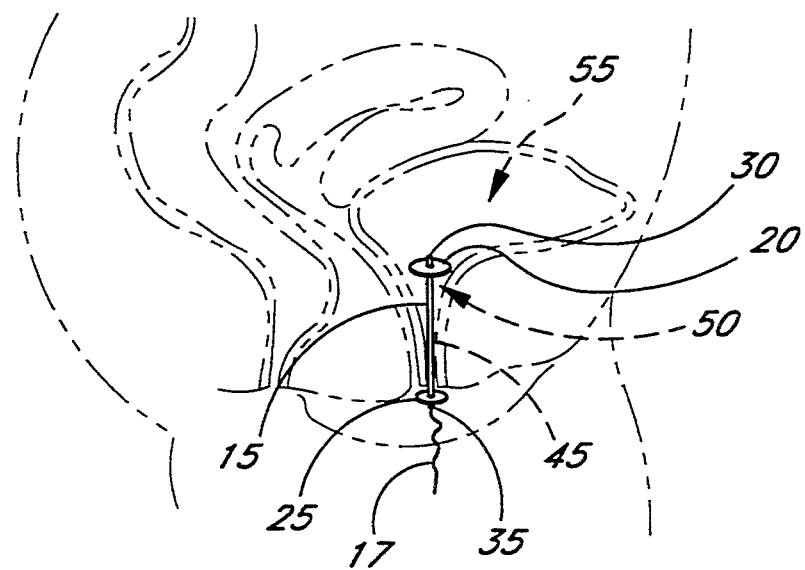
FIG. 4 is a schematic diagram showing the device positioned within the female urinary tract.

Referring to FIG. 4, the device is inserted by the individual into the urethra 45 with disc 20 entering first using the projection 30 as a guide. Once the device is inserted, disc 20 collapses like an umbrella, then flattens out once it has entered the bladder 55. The flexibility of disc 20 which allows it to collapse during insertion will reduce patient discomfort and will lessen the chance of irritating bladder neck 50 and the wall of urethra 45.

Disc 25 sits just outside the urethra 45 and prevents the device from migrating upward into the bladder 55. The diameter of the stem 15 is such that it does not contact the walls of the urethra 45 upon insertion, removal or when the device is resting inside the bladder 55, thus minimizing the possibility of urethral irritation. However, the stem 15 is thick enough to maintain its structural integrity upon insertion and removal of the device.

In an alternative embodiment, the device can be inserted with disc 25 entering first. In this case, the string 17 will be attached to projection 35 in place of projection 30. The dual disc design increases the flexibility of the device, since the individual will be able to insert into the bladder whichever disc is more effective in forming a seal to prevent the leakage of urine.

In yet another alternative embodiment, an embedded string extends beyond both of the two projections, and is cut by the user at one end, thereby allowing the individual to insert into the bladder whichever disc is more effective in forming a seal to prevent incontinence.

As an alternative means for introduction of the device, a sheath of sufficient diameter to allow passage of the device, but not large enough to irritate the urethra, is inserted into the urethra, leaving a small portion outside. The device can then be inserted into the sheath, either manually or with a plunger, with the larger disc inserted first. The sheath is then removed, leaving the device inside the urethra with the smaller disc remaining outside.

During an episode which causes tensing of the abdominal muscles, herein referred to as a stressful episode, pressure forces the device downward against the neck of the bladder, forming a seal to occlude the bladder neck, thus preventing the leakage of urine. The device thus occludes the bladder neck only during stressful episodes; at other times it simply sits inside the urethra with the larger disk resting on the bladder neck. The device applies minimal pressure to the bladder neck and urethra when not acting as a seal, and applies just enough pressure (equal to the pressure in the bladder) to preserve continence during a stressful episode. Since the stem does not occlude the urethra, it does not participate in continence; it mainly serves a guidance and support function. Since the device does not exert pressure on the walls of the urethra, the chance of urethral irritation and urethral dilation with associated leakage around the device is greatly minimized.

The disc shape of the ends of the device is important for preventing the device from migrating into or out of the bladder as compared to a more spherical or elliptical shape. The taper on an elliptical or spherical device could lead to a dilation of the bladder neck or urethra, resulting in potential migration of the device. One particular advantage of the device of the preferred embodiment is that it lacks on such taper. The lack of any taper on this preferred device together with its abrupt transition from the diameter of the stem to the disc makes migration virtually impossible.

The device is ordinarily inserted after voiding of urine, for example, prior to a social engagement. When the individual feels the urge to void, the device is removed by pulling on the smaller disc or on the string attached to the disc. During removal, the larger disk folds upwards, similar to an inverted umbrella, allowing for easy passage of the device through the urethra.

Advantageously, the device can be cleaned with soap and water prior to reinsertion. Alternatively, the device can be disposed of and a new device inserted when desired. The disposability of the device is feasible due to its simple, one-piece design and low manufacturing cost. Another particular advantage of the device is its lack of moving parts, grooves or chambers, present in prior art devices, which bacteria can colonize. This can lead to an increased frequency of urinary tract infections in the prior art devices since it is impossible to keep the moving parts, grooves and chambers free of bacteria. Since the instant device can be thoroughly disinfected, the potential of urinary tract infection is greatly minimized. The lack of moving parts also makes the device durable and cost effective to produce. The lack of valves and moving parts also ensures that the device will not undergo mechanical failure, a problem associated with prior art anti-incontinence devices. Thus, the device of the present invention is not subject to expulsion or retention due to mechanical failure. In addition, the lack of moving parts such as pumps, valves and syringes will enable individuals with manual dexterity problems, such as arthritis, to easily use the device.

To determine the appropriate length of the device for each individual, a calibration device can be used. In a preferred embodiment, the calibration device can be substantially similar to the device itself. Such a calibration device includes a calibrated flexible stem of 1–6 cm attached to two flexible discs. The calibration device is inserted until the larger disc enters the bladder, at which time the resistance will decrease since the disc is no longer within the urethra. The distance is then determined by reading the mark on the stem. In an alternative embodiment, the entire device can be inserted. The device is then retracted by pulling on the smaller disc until resistance is felt when the device just enters the urethra. The distance is then determined by reading the calibration mark.

To determine the efficacy of the device, a pilot clinical study is performed as described in the following example.

EXAMPLE

Clinical Study Using Incontinence Device

For inclusion in the study, the individual must be a female with incontinence, must be able to insert and remove the device, must not have a urinary tract infection and cannot be pregnant.

Each patient is given a preoperative evaluation including history of urinary disorders, urinalysis and urine culture. The patient is then given the pad weight test, a clinical assessment of stress incontinence. This assessment involves having the patient void followed by introduction of a volume of liquid into the bladder through a catheter. An absorbent pad is then attached to cover the urethral opening. The patient then performs a physical actively, after which time the pad is weighed to determine the amount of liquid involuntarily voided. The patient is also subjected to cystoscopy to determine whether the interior of the bladder is normal. A series of tests called urodynamic studies is also performed to obtain an overall assessment of bladder function. A questionnaire is also administered to determine level of incontinence, frequency, urgency, and other relevant information.

The device is then given to the subjects who immediately begin to use it as desired. The subjects return for office visits at, for example, 1 month, 3 months and six months. A urine culture is performed at 1 and 3 months to determine frequency of infection, and a pad weight test is performed at 3 months to determine efficacy of the device in preventing stress incontinence. A significantly decreased volume of liquid voided in the presence of the device as compared to its absence, as well as no significant incidence of infection, will indicate the efficacy and safety of the device.

Although this invention has been described in terms of certain preferred embodiments and applications, other embodiments and applications that are apparent to those of ordinary skill in the art are also within the scope of this invention. Accordingly, the scope of the invention is intended to be defined only by reference to the appended claims.

I claim:

1. A removable device for preventing involuntary urination in female patients, comprising:
   a flexible stem having a first end and a second end;
   a first flexible disc having a perimeter, a first face and a second face, said first face of said first disc attached to said first end of said stem;
   a second flexible disc having a perimeter, a first face and a second face, said first face of said second disc attached to said second end of said stem; and
   a projection attached to the second face of at least one of said discs.

2. The device of claim 1, wherein a string is attached to said projection.

3. The device of claim 2, wherein said string is longitudinally embedded within said stem and said projection, whereby said string extends beyond said projection.

4. The device of claim 1, wherein said projection is continuous with said stem.

5. The device of claim 1, wherein a projection is attached to the second face of each of said first and second discs.

6. The device of claim 4, wherein a string is attached to each of said projections.

7. The device of claim 1, wherein said device is made of a flexible, biocompatible material.

8. The device of claim 7, wherein said material is resistant to degradation by urine.

9. The device of claim 7, wherein said biocompatible material is an elastic polymer.

10. The device of claim 9, wherein said polymer is Kraton G, silicone or polyvinylchloride.

11. The device of claim 7, wherein said stem is more flexible along its lateral axis than along its longitudinal axis.

12. The device of claim 1, wherein said first disc is greater in diameter than said second disc.

13. The device of claim 1, wherein the diameter of said first disc is between about 1.0 cm and about 2.0 cm.

14. The device of claim 13, wherein the diameter of said first disc is 1.5 cm.

15. The device of claim 1, wherein the diameter of said second disc is between about 0.5 cm and about 1.5 cm.

16. The device of claim 15, wherein the diameter of said second disc is 1.0 cm.

17. The device of claim 1, wherein said discs are attached to said stem at their centers.

18. The device of claim 1, wherein said stem joins said discs at right angles.

19. The device of claim 1, wherein the length of said stem is between about three and about six centimeters.

20. The device of claim 1, wherein the diameter of said stem is about 0.4 cm.

21. A method of preventing incontinence in female patients, comprising:
   inserting an anti-incontinence device into the urethra of said patient so as to form a seal to occlude the bladder neck of said patient, said device comprising:
      a flexible stem having a first end and a second end;
      a first flexible disc having a perimeter, a first face and a second face, said first race of said first disc attached to said first end of said stem;
      a second flexible disc having a perimeter, a first face and a second face, said first face of said second disc attached to said second end of said stem; and
      a projection attached to the second face of at least one of said discs.

22. The method of claim 21, further comprising the step of removing said device prior to voiding of urine.

23. The method of claim 22, wherein said device additionally comprises a string attached to one of said projections, and wherein the removing step comprises pulling on said.

24. The method of claim 23, wherein said device comprises a projection on each of said discs and a string attached to each of said projections, and wherein the method additionally comprises cutting one of said strings prior to the inserting step.

* * * * *